United States Patent [19]
Chipian et al.

[11] Patent Number: 5,642,994
[45] Date of Patent: Jul. 1, 1997

[54] TEETH CLEANING IMPLEMENT WITH INTEGRATED FLUID DISPENSER

[75] Inventors: E. Terry Chipian, Sandy; Eric Simon; Alexander Theodore, both of Salt Lake City, all of Utah

[73] Assignee: Propheze, Inc., Salt Lake City, Utah

[21] Appl. No.: 494,838

[22] Filed: Jun. 26, 1995

[51] Int. Cl.⁶ .............................. A61C 1/10; A61C 1/12; A61C 17/02
[52] U.S. Cl. .......................................................... 433/82
[58] Field of Search ............................ 433/80, 82, 87, 433/89

[56] References Cited

U.S. PATENT DOCUMENTS

| | | |
|---|---|---|
| 2,400,912 | 5/1946 | Britt et al. |
| 2,738,528 | 3/1956 | Fridge, Sr. |
| 3,775,849 | 12/1973 | Condon |
| 3,987,550 | 10/1976 | Danne et al. |
| 4,173,828 | 11/1979 | Lustig et al. ............... 433/87 |
| 4,220,446 | 9/1980 | Walker ....................... 433/88 |
| 5,062,796 | 11/1991 | Rosenberg ................. 433/82 |
| 5,275,558 | 1/1994 | Seney ........................ 433/82 |

FOREIGN PATENT DOCUMENTS

1056339  1/1967  United Kingdom ................. 433/87

*Primary Examiner*—Nicholas D. Lucchesi
*Attorney, Agent, or Firm*—Thorpe North & Western, L.L.P.

[57] ABSTRACT

A fluid storage and dispensing container for cleaning teeth, which includes a modified prophy angle headpiece that attaches to existing hand-held prophy cup dental instrument handpieces. The headpiece has an integrated passage through the headpiece by which a fluid is dispensed from the fluid container to the rotatable prophy cup. The headpiece has a lumen through the angle that won't tear or close under flow pressure. The headpiece has a shelf on a top surface for guiding placement of the fluid container, and a snap-fit retaining clip at a base of the headpiece for securing a plurality of different fluid containers. A preferred embodiment of a fluid storage container is a flexible tube that is depressed by a finger or thumb to dispense a fluid such as prophylactic paste or a polishing lubricant to the prophy cup.

36 Claims, 8 Drawing Sheets

TEETH CLEANING IMPLEMENT WITH INTEGRATED FLUID DISPENSER

BACKGROUND OF THE INVENTION

1. Field of the Invention

This invention pertains to dispensing of a fluid from a dental instrument. More particularly, a cleaning agent such as prophylactic paste is dispensed from a manually controlled dispenser coupled to conventional hand-held tooth cleaning implements, enabling one-handed application of a tooth cleaning agent to the patient's teeth from the dental instrument without having to remove the instrument from the patient's mouth.

The tooth cleaning agent or other fluid is dispensed from a storage container that is integrated with a prophy angle headpiece. The headpiece is coupled to the dental instrument handpiece which supplies the mechanical force required to rotate the prophy cup.

2. Prior Art

Application of a fluid cleaning agent such as a prophylactic paste to a patient's teeth by an oral hygienist or a dentist is a common part of professional teeth cleaning. Typically, a prophy cup mounted on the end of a headpiece coupled to a dental instrument handpiece is dipped into a prophylactic paste-filled container to fill the cup. A portion of the headpiece and possibly a portion of the instrument handpiece is placed in the patient's mouth while the prophy paste-filled cup is pressed against the patient's teeth. The prophy cup is rotated by a system of gears in the headpiece that is coupled to a pneumatic actuation mechanism in the instrument handpiece. The paste is used rapidly, thus the prophy cup must be withdrawn from the patient's mouth and returned to the paste container often for refilling. The cleaning process is unnecessarily complicated and prolonged by the repeated refilling of the prophy cup.

Efforts have been made in the prior art to develop an apparatus capable of shortening the cleaning process. Typically, such efforts have concentrated on elaborate teeth cleaning prophy angle headpieces, new instrument handpieces, or a combination of the two. These devices generally include some type of paste container integrated with the dental instrument itself, and an apparatus for delivering paste from a container to the prophy cup. The prior art is typically represented by U.S. Pat. Nos. 2,400,912, 2,738,528, 3,775,849, 3,987,550, 4,220,446 and 5,062,796.

The aforementioned patents exemplify most of the elements of the prior art which partially explains the lack of success of any of these prophylactic paste dispensing prophy angle devices. For example, U.S. Pat. No. 2,738,528 might appear similar to the present invention because it shows a flexible paste-filled container strapped to the top of a headpiece. However, while the design is appealing because of its simplicity, close examination of the implementation readily accounts for its flawed performance which make it impractical for actual use. The design shows a flexible tube bent so as to allow paste in a collapsible dispenser to be manually propelled through a flexible tube by passing through the prophy cup headpiece and into the prophy cup. The tube is prone to kinking because the angle down into the headpiece is made of flexible material, interrupting paste flow and delaying cleaning. Using the container tubing as the path down through the headpiece for the cleaning agent also results in a loss of volume, thereby decreasing usable inside diameter of the lumen which can lead to increased flow resistance. The container tubing will also cause friction between the tube and the rotating shafts, especially if the tubing is an elastomeric material. Also, the shape of the paste container is round, having no surface for stabilizing the container when pressed, making it unwieldy and difficult to handle as it would twist from side-to-side. In addition, the anchoring system is a single strap that can be dislodged when the container is emptying, making the device even more awkward to use. Finally, the container as embodied would have to be filled from the narrow lumen end, thus leading to increased difficulty and cost of the system.

U.S. Pat. No. 4,220,446 is a good illustration of how prior art designs are often bulky and ill-suited for being inserted in or near the patient's mouth without interfering with an operator's view or instrument access to the mouth. It also requires a secondary pneumatic source for dispensing of the paste, further complicating the design. Finally, the instrument only dispenses paste to the side of the cup, not in it as desired.

Far more common in the prior art are major modifications to the dental instrument handpiece itself. U.S. Pat. Nos. 5,062,796, 3,987,550, 3,775,849 and 2,400,912 illustrate such redesigns of the instrument handpiece. The handpiece typically incorporates a pneumatic pressure system for driving paste from a container and into a prophy cup. The major drawback to such designs is the retooling that dental instruments already installed would require, as well as the cost of an elaborate device that would now be prone to break because of the additional moving parts. Some of these designs even include foot-pedals or other elaborate actuation and control means that unnecessarily complicate the instrument design. By constructing the dispensing container inside the handpiece, the device is no longer disposable. The entire device must be cleaned and sterilized before each use. Furthermore, it is more difficult to change cleaning agents during the procedure if required. The fact that these designs are not in use today demonstrates their impracticality.

If implemented correctly, integrating a paste supply with the instrument handpiece overcomes the problem of having an instrument small enough not to interfere with the cleaning process. However, the addition of a mechanism for delivering the paste from the container to the prophy cup complicates the design and increases costs to such a degree, as demonstrated by the lack of any such device that the inventors are aware of on the market, to make the concept impractical.

Accordingly, the challenge in designing a dispensing system for fluid substances such as the prophy paste that would be an improvement over the prior art is to provide a device that uses existing dental instrument handpieces without having to redesign them for fluid storage or dispensing. It would also be an improvement to provide a device that is simple to use, doesn't interfere with visual or instrument access to a patient's mouth, provides easily replaceable fluid containers, and offers a variety of different fluid dispensers for a user to choose from while providing a disposable headpiece that at a low cost.

OBJECTS AND SUMMARY OF THE INVENTION

It is an object of the present invention to provide a dispenser for fluid substances such as prophylactic paste or other fluid agent that utilizes existing hand-held tooth cleaning dental instruments without the need to retrofit existing instrument handpieces.

It is another object of this invention to provide simple manual dispensing of a fluid agent.

It is yet another object of the present invention to provide a variety of different manually actuated fluid agent containers for a user to choose from.

It is a further object of the invention to provide fluid agent containers that are disposable and easy to replace.

It is yet a further object of the present invention to provide a prophy angle that will not interfere with viewing or physical access to the patient's mouth when a fluid agent container is ready for dispensing.

It is still a further object of the invention to provide a fluid agent dispensing and storage container which is capable of dispensing a variety of fluid agents including abrasive pastes, polishing compounds, lubricants, bleaching agents, bonding agents and etchants.

These and other objects are realized in a fluid agent dispensing system for teeth cleaning that includes a modified prophy angle headpiece that attaches to existing hand-held prophy cup dental instrument handpieces. The headpiece has an integrated passage for paste to travel from the fluid agent storage container to the rotatable prophy cup. The rigid lumen which produces an angled path for the fluid agent flowing through the headpiece won't tear or close under pressure. The headpiece has a shelf for guiding placement and increasing stability of the fluid container, a secure yet reversible means for attaching a container orifice to a headpiece inlet lumen, and a snap-fit retaining clip at the base of the headpiece for securing a plurality of different fluid agent containers.

These and other objects, features, advantages and alternative aspects of the present invention will become apparent to those skilled in the art from a consideration of the following detailed description taken in combination with the accompanying drawings.

DETAILED DESCRIPTION OF THE INVENTION

Reference will now be made to the drawings in which the various elements of the present invention will be given numerical designations and in which the invention will be discussed so as to enable one skilled in the art to make and use the invention.

Figure 1A:
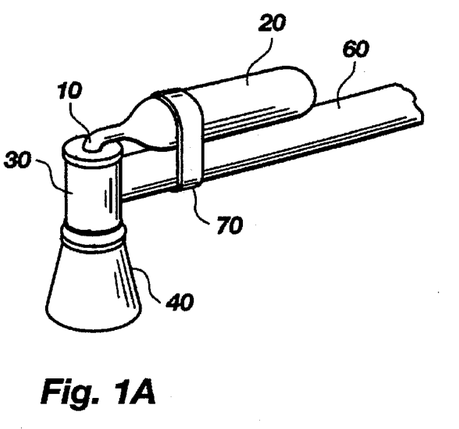
FIG. 1A is a perspective view of a dental instrument of the prior art.
Figure 1B:
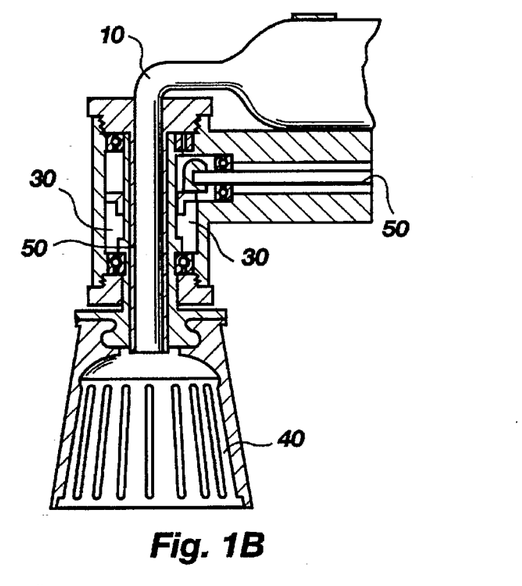
FIG. 1B is an elevational partially cross-sectional close-up view of the cleaning end of the dental instrument shown in FIG. 1A.

FIGS. 1A and 1B offer two views of a same prior art system for dispensing a fluid-like agent for teeth cleaning. It should be remembered that while a teeth cleaning agent is almost exclusively disclosed herein, other fluid-like substances may be stored and dispensed using the present invention. However, in a preferred embodiment, a teeth cleaning agent most often referred to is a prophylactic paste, or prophy paste as it is commonly known. FIG. 1A is a perspective view of the simple system that the inventors believe is probably the most similar in appearance to the present invention, but which fails to accomplished the task for which it was designed. As explained previously, U.S. Pat. No. 2,738,528 shows a flexible lumen 10 bent so as to allow paste in a collapsible dispenser 20 to be manually dispensed through the lumen 10 by passing through the prophy cup headpiece 30 and into the prophy cup 40. The lumen 10 is prone to kinking because the material is likely made of a flexible elastomeric material. Using a lumen 10 as the path down through the headpiece 30 results in a decrease of usable inside diameter of the lumen 10, increasing fluid agent flow resistance. The lumen 10 will also cause friction between the lumen 10 and rotating shafts 50 (see FIG. 1B).

No stabilizing surface 60 for the container 20 makes the instrument unwieldy and difficult to handle. In addition, the single strap 70 anchoring device can be dislodged while the container 20 is emptying. Finally, the container 20 would have to be filled from the narrow lumen 10 end because of the design of the container 20, increasing cost and difficulty.

Figure 2A:
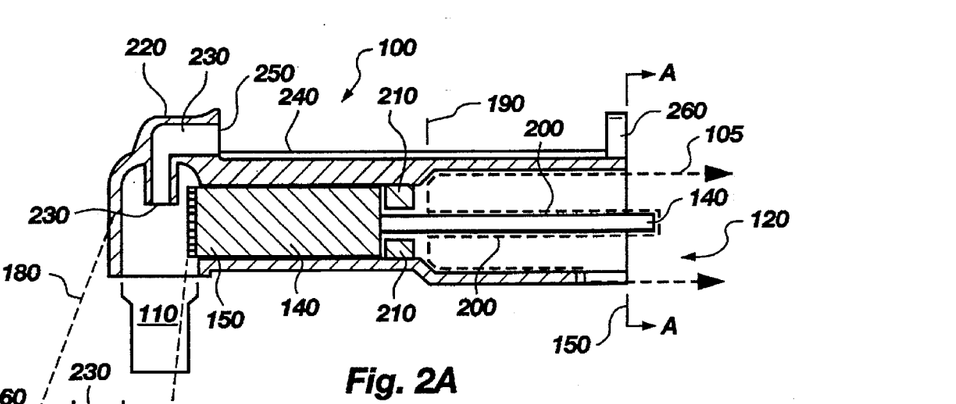
FIG. 2A is an elevational partially cross-sectional view of the prophy angle headpiece made in accordance with the disclosure of the present invention.

FIG. 2A begins to illustrate elements of a preferred embodiment which overcomes the drawbacks of the prior art shown in FIGS. 1A and 1B, while retaining the desired simplicity of the design. All the embodiments to be disclosed herein share a common prophy angle headpiece, and differ only in the design of the fluid agent storage container and the method of dispensing the fluid agent from the container to the prophy cup. Therefore, the common headpiece will first be described in detail to illustrate several of the novel features. The different fluid agent storage containers will be described afterwards, beginning with a preferred embodiment.

FIG. 2A is an illustration an elevational cross-sectional view of the prophy angle headpiece 100 of the present invention. The headpiece 100 is the disposable portion of a teeth cleaning instrument 105 (shown in dashed outline only). A rotatable prophy cup 110 on the end of the headpiece 100 is dipped into a prophylactic paste in a paste container near the instrument.

As shown, the headpiece 100 is a hollow tube-like passage having a central bore 120 therethrough. Extending through a long section of the bore 120 is a drive shaft 140 protruding from an attaching end 150 of the headpiece 100 where the instrument handpiece 105 couples to the headpiece 100 and the drive shaft 140. At the opposite end of the drive shaft 140 is a spindle gear 150 that meshes in geared engagement with a nib gear 160 (see FIG. 2B) of a cup shaft 170 (see FIG. 2B). The bore 120 makes a ninety degree turn at the point of geared engagement, such that the cup shaft 170 is at right angles to the drive shaft 140, and protrudes from a cleaning end 180 of the headpiece 100.

The attaching end 150 of the headpiece 100 partially surrounds the instrument handpiece 105 up to a point 190 where the bore 120 narrows within the headpiece 100, while the drive shaft 140 is enclosed by a gripping surface 200 within the instrument handpiece 105. The instrument handpiece 105 is commonly locked into place by twisting to tighten the gripping surface 200 around the drive shaft. The drive shaft 140 is held securely within the headpiece 100 by projections 210 extending outward perpendicular to the bore 120 walls, preventing the drive shaft 140 from being pulled from the headpiece 100.

Along an axis 220 defined by the cup shaft 170 is the end of a circular lumen 230 which partially protrudes into the central bore 120 from a headpiece shelf 240. The cup shaft 170 fits around this lumen 230 (see FIG. 2B) which acts as a bearing to help secure the cup shaft 170 so that it does not hit the sidewalls of the bore 120 when the spindle gear 150 presses against the nib gear 160. The partially protruding lumen 230 extends from the central bore 120 of the headpiece 100 through an angle onto the headpiece shelf 240 (see FIG. 2C). In a preferred embodiment, the headpiece lumen 230 makes an interference taper or 0.060 inch/inch taper after the angle, and then ends at a container port 250. The fluid agent storage container (not shown) is secured by interference fitting a tapered orifice (not shown) inside the port 250, and then securing the end of the storage container to the headpiece 100.

It is possible that other types of connecting ports 250 could be used to secure the orifice of a fluid agent storage container. For example, the port 250 could provide locking rings, threads, or snaps. However, the tolerance of the parts used in constructing the cleaning agent storage container and the headpiece 100 are such that an interference fit provides sufficient tension so as to securely hold the container orifice, as well as prevent reflux of fluid agent at the port 250.

The headpiece 100 has an integrally formed shelf 240 on a top surface. The shelf 240 forms a depression or trough on the top surface of the headpiece 100, the raised edges of the shelf 240 helping to keep the fluid agent storage container stable when pushed or pressed to eject a cleaning agent. At the end of the shelf 240 directly above the headpiece attaching end 150 are two slightly flexible fluid agent storage container securing pins 260 (see FIG. 2C) projecting perpendicular to the shelf 240. These securing pins 260 are used to attach a variety of fluid agent storage containers to be described herein.

A description of the components in the central bore 120 is completed by describing the cup shaft 170 (shown in FIG. 2B) and connecting prophy cup 110. The cup shaft 170 has a hollow bore 270 through which flows the fluid agent from the storage container to the prophy cup 110. Unlike some prior art headpieces, the nib gear 160 is above the spindle gear 150 relative to the prophy cup 110. This arrangement enables the cup shaft 170 to be held securely in place without a cap or other device being required on the headpiece 100 to hold the cup shaft 170 in place. In other words, the cup shaft 170 is prevented from falling out of the cleaning end 180 of the headpiece 100 because the nib gear 160 is supported by the spindle gear 150.

Figure 2B:
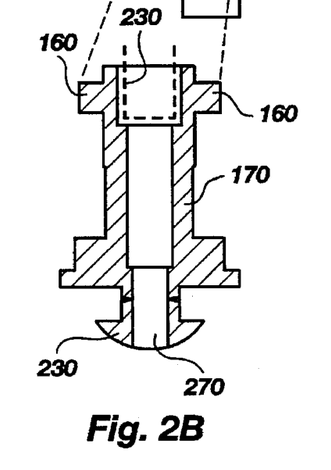
FIG. 2B is an elevational cross-section view of the cup shaft used in the headpiece of FIG. 2A.

Finally, the cup shaft 170 has a knobbed end 280 around which a rubberized prophy cup 110 stretches. The prophy cup 110 has a hole bored through it to allow the fluid agent to enter the prophy cup 110.

Figure 2C:
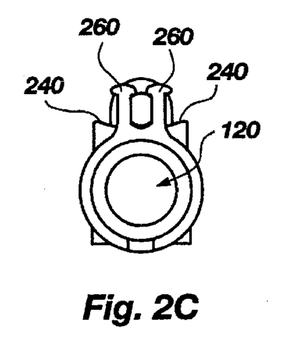
FIG. 2C is an attachment end view taken along the line A—A from FIG. 2A.
Figure 3A:
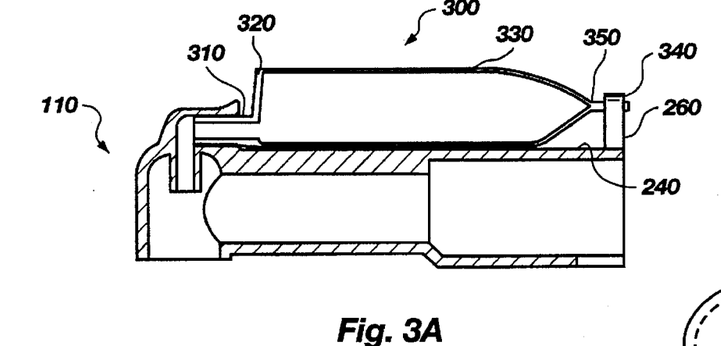
FIG. 3A is an elevational cross-section view of the bladder embodiment of fluid agent storage container fitted to the headpiece of FIG. 2A.
Figure 3B:
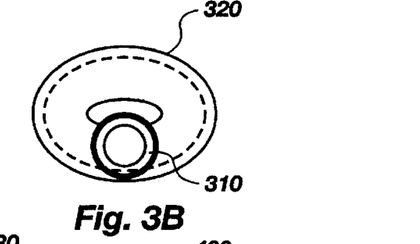
FIG. 3B is an elevational view of the cap of the storage container as seen from the line B—B.

The present invention is a combination of the headpiece 100 described in FIGS. 2A, 2B and 2C, and a fluid agent storage container 300 shown in a preferred embodiment in FIGS. 3A and 3B. The storage container 300 is the simplest of all the storage containers to be disclosed herein. The container 300 is a flexible bladder, similar in function and form to a tube of toothpaste, except that a dispensing orifice 310 is offset from the center of an end cap 320 (see FIG. 3B). The end cap 320 need not be a rigid material, so long as the end cap provides the integrated orifice 310 a support surface on the bladder 330. The dispensing orifice 310 is a small tapered lumen likely to be composed of a firm thermoplastic or other rigid material. The orifice 310 is designed to fit snugly into the interference tapered container port 250 of the headpiece 110, and still allow a fluid agent to flow out of the container 300 and into the port 250. In a preferred embodiment, the rigid dispensing orifice 310 is integrally formed to the container end cap 320. The container end cap 320 has sealed to it what is likely but not necessarily a more flexible bladder 330 which is filled with the fluid agent. At a sealed end 350 opposite the end cap 320, the bladder 330 is pressed and heat sealed to form a slightly thicker flat surface from opposing bladder 330 sidewalls in which a die cut slot 340 is punched. The slot 340 is slightly smaller than the widest width of the securing pins 260 of the headpiece 110.

To dispense the fluid agent, the headpiece 100 is secured to the dental instrument handpiece 105. The dispensing orifice 310 of a fluid agent filled bladder 330 slides into the interference tapered container port 250. The bladder 330 rests on the headpiece shelf 240, and the die pressed slot 340 at the sealed end 350 of the bladder 330 is stretched over the securing pins 260. The dental instrument is now ready to use. A fingertip or thumb presses from the sealed end 350 of the bladder 330, thereby forcing a fluid agent out of the bladder 330 and into the headpiece lumen 230, through the cup shaft 170 and into the prophy cup 110. The dental instrument 105 is then actuated to pneumatically rotate the drive shaft 140 in the headpiece 100, causing the prophy cup 110 to rotate rapidly.

The preferred embodiment is a simpler design than the devices shown in the prior art. Some of the most important advantages such as that shown in FIGS. 1A and 1B, are that the lumen 230 carrying a fluid agent through the headpiece 110 is rigid to prevent kinks from developing and interrupting fluid agent dispensing, the usable diameter of the pathway is kept as large as possible by integrating the lumen into the headpiece, there is significantly reduced friction between the pathway and the spindle and nib gears, a shelf is provided to stabilize the container while being pressed, the fluid agent storage container is securely anchored when the container is full, empty or being pressed to discharge the fluid agent, and the storage container is filled with fluid agent and then sealed from a wide port, thus making the device less costly and easier to manufacture.

Prior art devices are mainly distinguished from the present invention by the fact that none are in use today because of the practical difficulties encountered when actually trying to dispense a fluid agent and integrating them with existing pneumatic handpiece designs.

Not yet addressed is the nature of the fluid agent used in the dispensing device of the present invention. It is envisioned that the fluid agent is the prophylactic paste already in use in the dental industry today. The paste provides a gritty material that removes build-up on teeth when applied with a rotating prophy cup. Although the paste is available in different levels of viscosity to provide different degrees of abrasive material for cleaning, it is possible that the paste may require some alterations in viscosity to enable a more rapid flow of paste through the headpiece lumen. Alternately, other types of fluid agents might be dispensed. For example, it may be advantageous to permanently embed the abrasive agent in the prophy cup material as shown if FIG. 11, in which case a lubricant could be dispensed through the cup to reduce frictional heating and increase cleaning efficiency. Furthermore, other fluid-like agents such as bleaching agents, bonding agents, primers, or etchants might be dispensed in similar fashion for a variety of purposes.

Figure 4A:
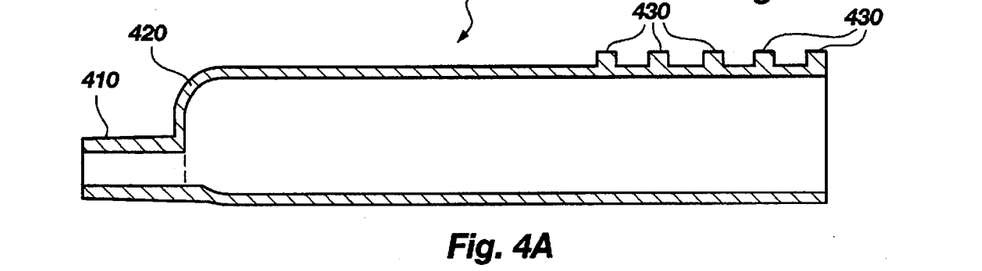
FIG. 4A is an elevational cross-section view of the alternate syringe embodiment of the fluid agent storage container.

FIG. 4A shows the fluid agent storage container 400 in an alternate embodiment that has a rigid body as opposed to the soft-sided bladder of the preferred embodiment. The container 400 is essentially a modified syringe. The modifications allow the container 400 to couple to the interference tapered attachment port 250 of the headpiece 100 by offsetting the dispensing orifice 410 from the center of a syringe end cap 420 to an edge of the end cap, much like the preferred embodiment in FIG. 3B. Another modification is that the body of the syringe can be flattened to provide an oval or ellipsoid cross-section to better fit the container to the shape of the shelf 240 on top of the headpiece 100 and reduce profile height. Relative to the top of the headpiece 100, the syringe 400 might have a finger grip 430 to prevent a finger from sliding off the syringe 400, not when squeezing out a fluid agent, but when applying pressure with the instrument handpiece to a patient's teeth.

Figure 4B:
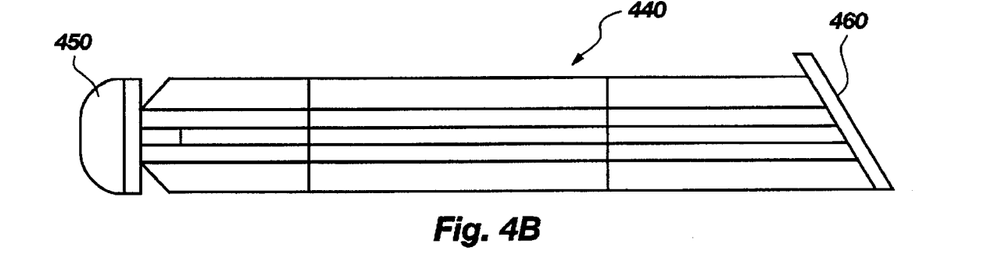
FIG. 4B is an elevational view of the plunger used in the syringe of FIG. 4A.

FIG. 4B shows the plunger 440 of the syringe 400 which has a wiper 450. Wipers are typically rubber tipped so as to provide a seal around the wiper edges to prevent reflux of material being dispensed by the syringe 400. However, tolerances of the syringe 400 and wiper 450 are likely to be such that a rubber seal will be unnecessary. Therefore, the plunger 440 in the present invention preferably uses an integral wiper 450. The seal between the wiper and the syringe body 400 is not likely to prevent all reflux, but it will be sufficient such that reflux of a fluid agent is immaterial. Finally, a pushing end 460 of the plunger 440 will have an appropriate surface against which a finger or thumb is pressed. As shown, the pushing end 460 has been designed to be slanted to provide a more comfortable angle for a finger or thumb tip to press against.

Figures 4C, 4D:
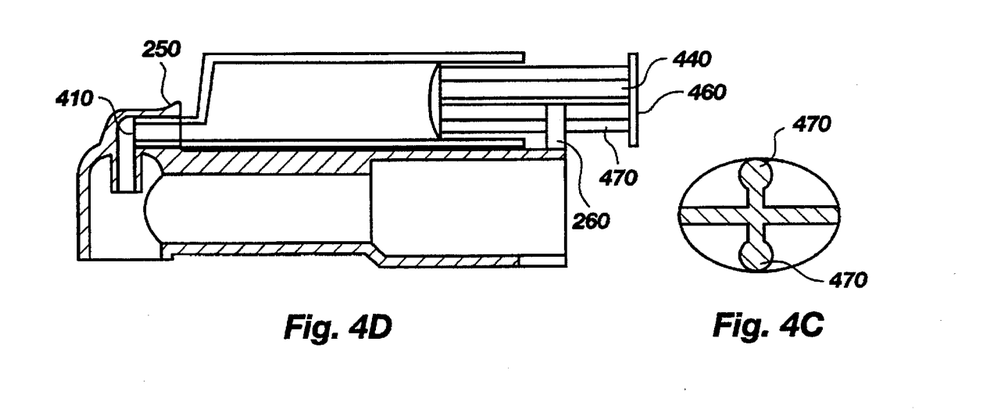
FIG. 4C is an elevational view of a cross-section of the plunger as shown in FIG. 4B.
FIG. 4D is an elevational cross-section view of the complete syringe embodiment of the fluid agent storage container fitted to the headpiece of FIG. 2A.

To reduce the volume of materials used in making the plunger 440, the length of the plunger 440 is ribbed, as shown in FIG. 4C, instead of being solid. Some advantages of the rib design are to provide a beaded edge sliding surface 470 around which the securing pins 260 of the attachment end 150 of the headpiece 110 can be secured. Thus, the headpiece 110 does not attach to the body of the syringe 400, but rather to the plunger 440. In this way the plunger is both securely attached to the headpiece and longitudinally guided into the syringe bore. This cross-sectional view shown in FIG. 4C of the plunger 440 shows two beaded edges 470 around which the securing pins 260 can snap. Although shown with an upper and lower beaded edges 470, it is likely that only the lower beaded edge will be needed. Such universal design eliminates the need for providing another attachment mechanism for each different fluid agent storage container. The securing pins 260 of the headpiece 110 provide the only attaching mechanism required.

To dispense a fluid agent from the syringe device, the headpiece 110 is secured to the dental instrument handpiece (not shown). As illustrated in FIG. 4D, the dispensing orifice 410 of a fluid agent storage container (syringe 400) is inserted into the interference tapered attachment port 250, while the ribbed plunger surface 470 is snapped into the space between the securing pins 260. The device is now ready to use. A finger or thumb tip presses on the angled pushing end 460 of the plunger 440 to dispense a fluid agent into the prophy cup 110. The dental instrument (not shown) is then actuated to mechanically rotate the drive shaft 140 in the headpiece 110, causing the prophy cup 110 to rotate rapidly.

Figure 5A:
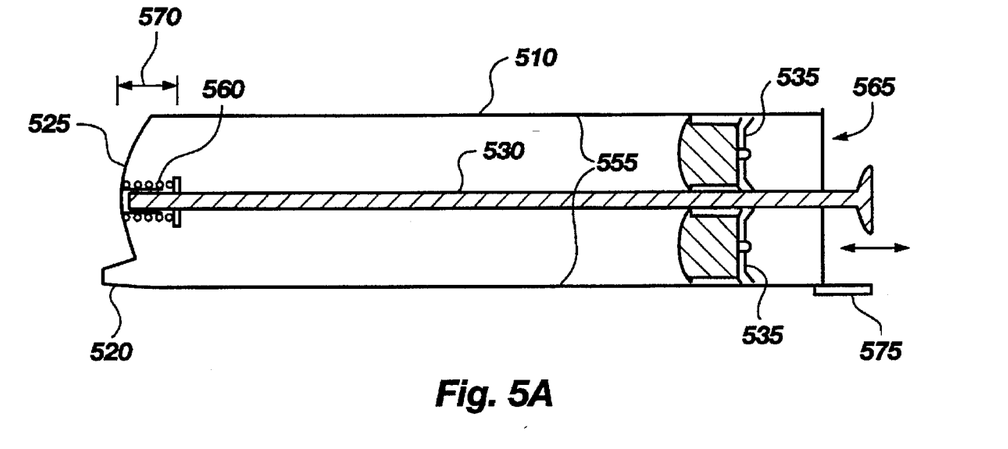
FIG. 5A is an elevational cross-section view of an alternative embodiment of the syringe device shown in FIGS. 4.

FIG. 5A shows another alternative embodiment of the fluid agent dispenser of the present invention. Like the syringe embodiment of FIG. 4, the body 510 of this modified syringe is rigid. The same interference taper dispensing orifice 520 is offset from the center of the syringe face 525 for easy attachment to the container port.

Figure 5B:
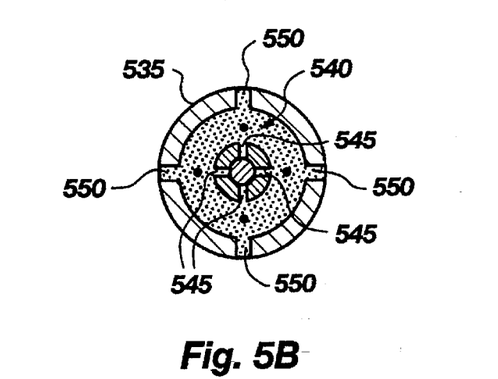
FIG. 5B is a plan view of the wiper and connected washer used in the plunger of FIG. 5A.

The syringe 510 is different from the previous syringe embodiment in the internal and plunger 530 structure. In this embodiment, the plunger 535 is not attached to the wiper 535. Instead, the floating wiper 535 is free to move forward towards the dispensing orifice 520 of the syringe 510, but can not backslide. Backslide motion is arrested by using a metal star washer 540 (FIG. 5B) coupled to the outer surface of the wiper 535. The washer 540 has both inner 545 and outer 550 teeth, where the inner teeth 545 grip the plunger barrel 530, and the outer teeth 550 grip the inner surface 555 of the syringe body. The plunger barrel 530 has fitted to the end within the syringe a spring 560. The spring 560 is fixed to the syringe body 510 and centered on the inside of dispensing face 525. It does not interfere with the dispensing orifice 520 because it is offset from the dispensing face 520.

The device shown in this embodiment operates as follows. The initial position of the wiper 535 is where it is pulled back as near to the opening 565 of the syringe body 510 as possible. However, unlike the first syringe embodiment, the plunger 530 is inserted almost entirely into the syringe 510. The plunger 530 can only be pushed a short distance 570 before the plunger 530 makes contact with the syringe dispensing face 525. When the fluid agent within the syringe 510 is to be dispensed, the plunger 530 is pushed until making contact with the dispensing face 525. The star washer inner teeth 545 gripping the plunger surface 530 forces the wiper 535 further inside the syringe body 510, pushing fluid agent out of the dispensing orifice 520. When the plunger 530 is released, the spring 560 inside the syringe 510 pushes the plunger 530 out of the syringe 510 to its original position. The star washer inner teeth 545 allow the plunger 530 to slide backward without being pulled because of the angle of the teeth 545, 550. The star washer outer teeth 550 are angled so as to grip the inner syringe surface 555 so that the wiper 535 does not move backward with the plunger 530. Whenever fluid agent is required in the prophy cup, the plunger 530 is repeatedly depressed until a sufficient quantity has been dispensed.

The plunger 530 is constructed without the ribbed structure of the embodiment of FIG. 4C, 470. Therefore, an alternative method of attaching the syringe 410 to the headpiece is found by creating an extension 575 from the body of the syringe 510 which snaps into place between the two restraining pins of the headpiece (not shown). The plunger 530 is sufficiently long so that the restraining pins do not interfere with the forward and backward motion of the plunger 530.

Figure 5C:
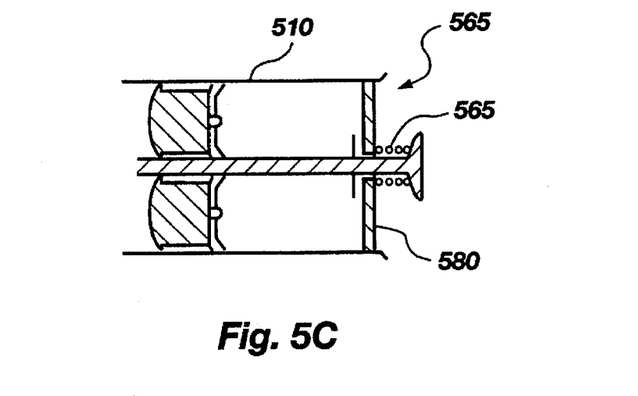
FIG. 5C is a close-up elevational cross section view of an alternative embodiment of the plunger shown in FIG. 5A.

A modification to the structure of FIG. 5A and shown in FIG. 5C would be to place an end cap 580 over the open end 565 of the syringe body 510, and then moving the spring 560 from inside the syringe 510 to outside the syringe body 510 so that it is positioned between the pushing end of the plunger 530 and the end cap 580. This configuration would reduce the structural bulk within the syringe 510, thereby allowing for more paste to be stored therein.

Figure 6A:
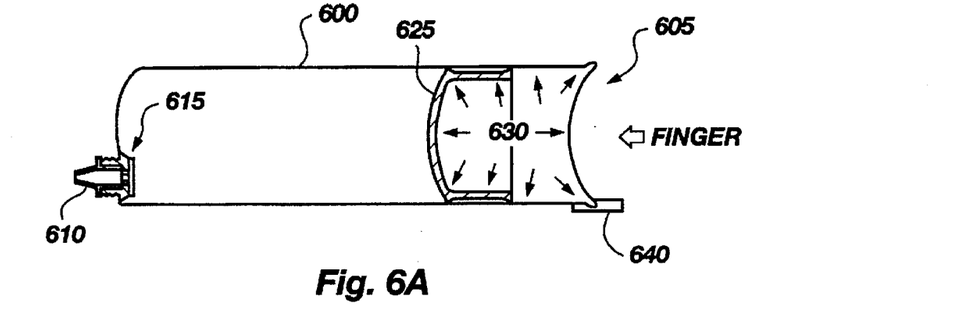
FIG. 6A is an elevational cross-section view of an alternative embodiment of a fluid agent storage container.
Figure 6B:
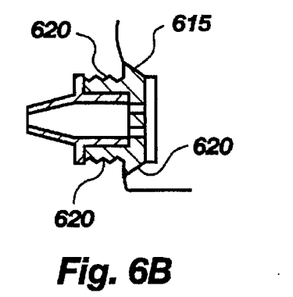
FIG. 6B is a close-up view showing detail of the dispensing orifice, valves and gasket.
Figure 6C:
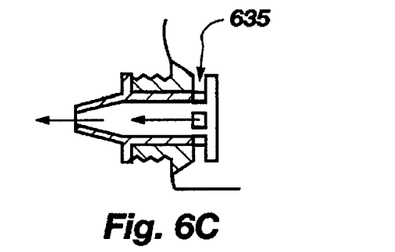
FIG. 6C is a close-up view showing detail of the objects of FIG. 6B, but in an actuated condition.

Another alternative embodiment of a fluid agent dispenser is shown in FIG. 6A. The body of the dispenser 600 is again a rigid structure, but unlike a syringe, the attachment end 605 is closed. On the outside, the dispensing orifice 610 has the familiar interference taper to fit snugly into the headpiece container port. However, internally the dispensing orifice 610 has a slightly modified structure. The orifice body 610 is rigid, having a base valve structure 615 inside the dispenser body, and wherein the entire orifice body moves in sliding engagement with the dispenser body 600. Surrounding the orifice body 610 is a bellows gasket 620 shown in FIG. 6B. The bellows gasket 620 is compressed when a finger or thumb pushes the entire dispensing body 600 forward toward the headpiece container port while the base valve 615 remains fixed. As the bellows gasket 620 is compressed, the base valve 615 within the dispensing body 600 is exposed as shown in FIG. 6C. At the attachment end 605 is a floating wiper 625. Behind the wiper 625 is a gas-filled space 630 under internal pressure. Exposing the base valve 615 enables the gas-filled space 630 behind the floating wiper 625 to expand, pushing the wiper 625 forward and dispensing fluid agent 635 through the dispensing orifice 610. When the dispensing body 600 is released, the bellows gasket 620 is forced back over the base valve 615 by the expanding gasket 620, stopping the flow of fluid agent 635.

The bellows gasket 620 is comprised of an elastomeric material that has sufficient strength to fully expand to cover the base valve ducts 615 when the dispensing body 600 is not being pressed forward. Like the embodiment of FIG. 5A, this embodiment attaches to the headpiece securing pins by way of a projection 640 at the attachment end 605 that snaps in place between the headpiece securing pins and slides forward and backward with the dispensing body 600.

Figure 7A:
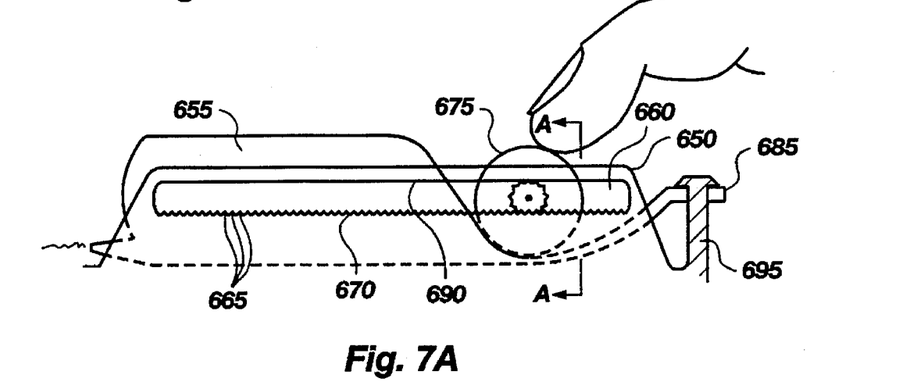
FIG. 7A is a elevational view of an alternative embodiment of FIGS. 3.
Figure 7B:
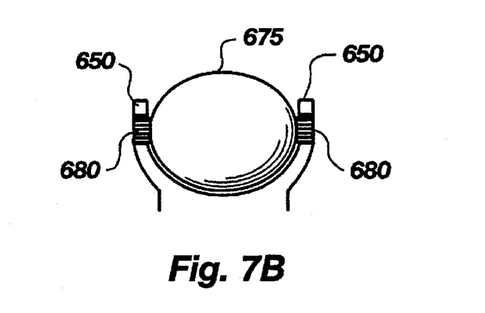
FIG. 7B is an elevational view of FIG. 7A from the perspective of A—A.

The alternative embodiment illustrated in FIG. 7A is a modification of the soft-walled bladder of FIG. 3A. The modification comes in the form of the headpiece shelf having higher retaining walls 650 wherein the dispensing bladder 655 rests. Each retaining wall 650 has a splined slot 660 along the long axis of the shelf, the slot 660 being near the top edge of the retaining walls 650. The splines 665 are only found on the bottom edge 670 of the slot 660. The other modification is the addition of an ellipsoid roller 675 that rests within the shelf and sidewalls 650, having projections 680 on opposite sides which fit in the retaining wall slots 660 which mesh in rolling engagement with the splines 665.

The initial position of the components of this embodiment has the roller 675 near the attaching end 685 of the bladder 655. A fluid agent is dispensed by pressing down and forward on the roller 675. The roller 675 acts to squeeze the fluid agent from the dispenser 655 more efficiently and thoroughly than a finger. This is accomplished because releasing the roller 675 does not cause it to slide backwards. Instead, the roller 675 stays in position by the slight pressure of the dispensing bladder 655 slightly lifting the roller 675 causing the roller splines 665 to catch against the upper slot surface 690. The roller 675 impedes backflow of fluid agent, thus making it unnecessary to begin pushing from the now empty end of the bladder 655. The splines 665 on the lower edge 670 of the slot 660 assist the roller 675 movement by preventing roller 675 slippage, similar to a rack and pinion system.

It is noted that this embodiment is more difficult to use because of the tight space that the roller 675 must squeeze into after anchoring the bladder 655 to the securing pins 695. Furthermore, while total usable dispensing volume may be slightly smaller than without the roller 675, fluid agent squeezed from the bladder 655 to make room for the roller 675 will not do much more than fill the passage through the headpiece to the prophy cup.

Figure 8A:
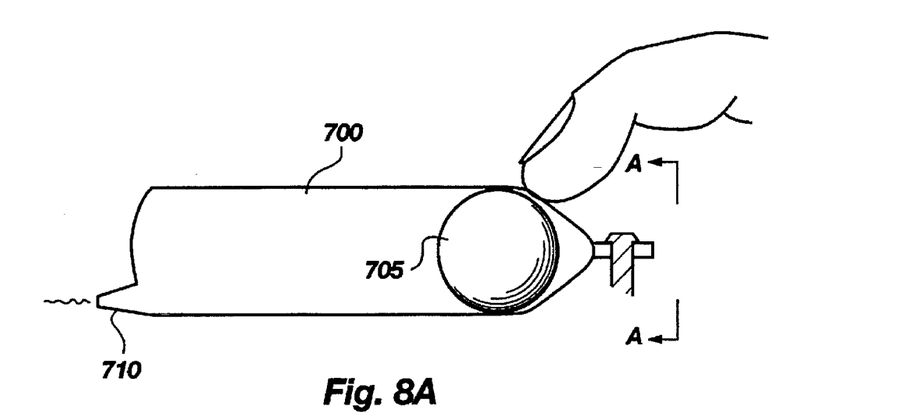
FIG. 8A is a elevational view of an alternative embodiment of FIGS. 3.
Figure 8B:
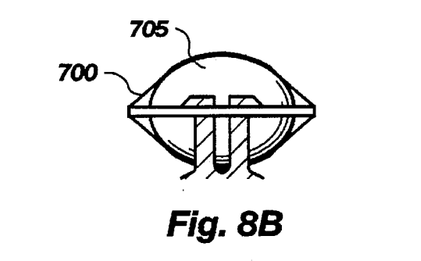
FIG. 8B is an elevational view of FIG. 8A from the perspective of A—A.

Another embodiment described herein is shown in FIG. 8A. This dispensing device 700 is a variation of the embodiment of FIG. 7A. As shown, an ellipsoid roller 705 is now inside the soft walled dispensing bladder 700. Finger pressure on the roller 705 pushes and rolls it inside the bladder 700, dispensing fluid agent through the dispensing orifice 710. While increasing efficiency of dispensing by more thoroughly pushing fluid agent from the bladder 700, the tradeoff is a loss of total volume inside the bladder 700, resulting in a smaller total delivery of a fluid agent.

Figure 9A:
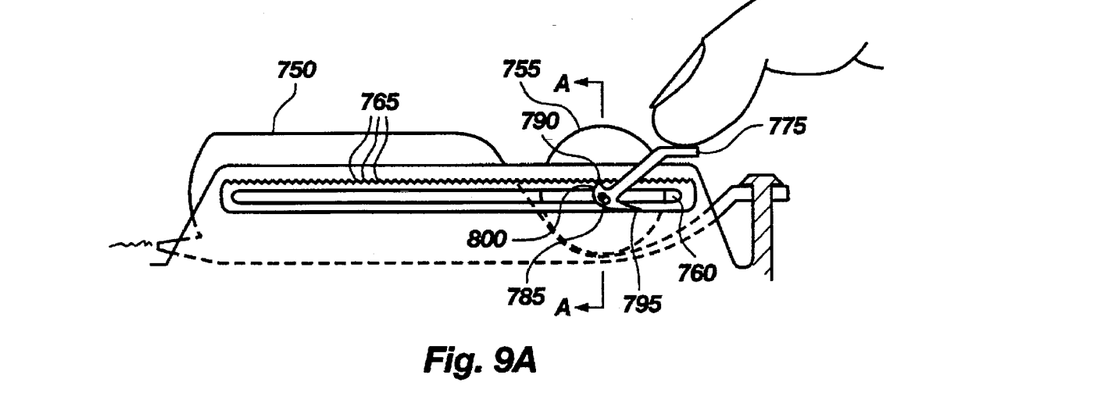
FIG. 9A is a elevational view of an alternative embodiment of FIGS. 3.
Figure 9B:
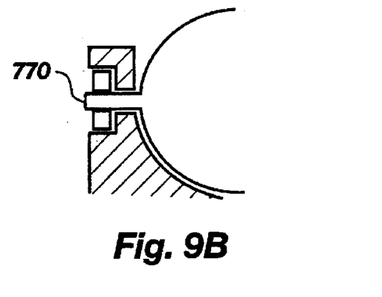
FIG. 9B is an elevational view of FIG. 9A from the perspective of A—A.
Figure 9C:
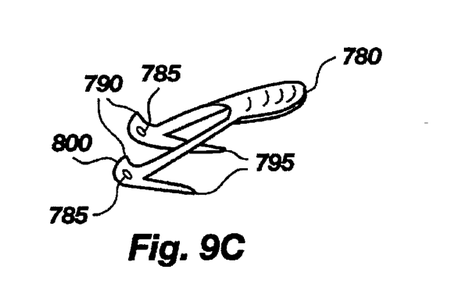
FIG. 9C is a perspective view of the lever arm of FIG. 9A.

An alternative embodiment of the dispensing container shown in FIG. 7A is a modification to the design as shown in FIG. 9A. However, instead of the splines 765 being on the lower slot 760 edge, the splines 765 are now on the upper slot 760 edge. Furthermore, the roller with the splined axis of FIG. 7A is replaced with a roller 755 having a smooth axis 770. Coupled to the axis 770 on both ends of the roller 755 is a finger lever 775 in the form of an arch 780 as shown in FIG. 9C. The end of each arch 780 has a working end with a hole 785 through it to accommodate the roller axis 770. The working end also has a lever tooth 790 for engaging the splines 765 in the sidewall slot 760, and a leaf spring 795.

At rest, the lever tooth 790 of the working end is engaged with a spline 765, keeping the roller 755 from sliding backward. When pressure is applied to the lever arm 775, the pivot point 785, or the point where the working end mates with the roller axis 770, moves forward. A spline 765 is now in contact with a pivot surface 800 of the working end. When the lever arm 775 is released, the leaf spring 795 engages the track 760 which causes the spline 765 to slide across the pivot surface 800 forcing the working end forward until the lever tooth 790 falls into place between splines 765 forward of its previous location.

Figure 10:
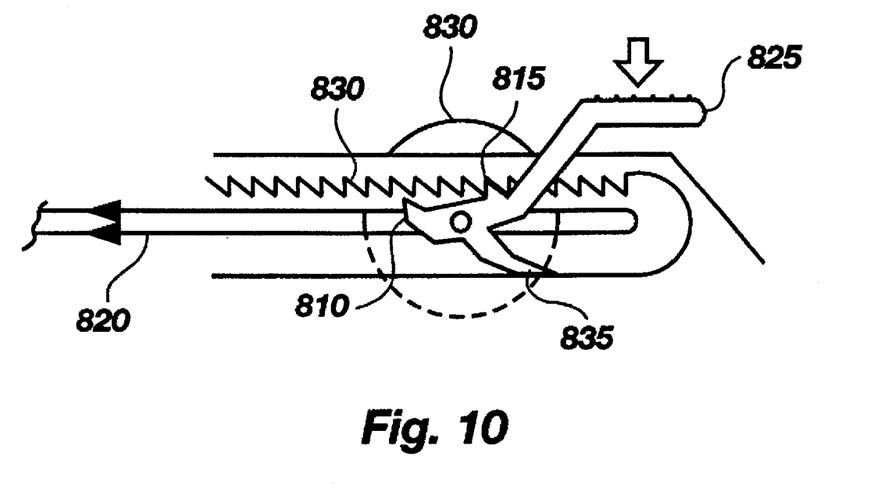
FIG. 10 is an elevational view of an alternative embodiment of FIG. 9A.

Another alternative embodiment of the fluid agent dispenser is shown in FIG. 10. This design is a modification of the embodiment of FIG. 9A. The differences are that now there are forward 810 and rear 815 lever teeth, as well as a tension device 80 that pulls the lever arm 825 and connected roller 830 forward.

The principle of operation is much the same as in FIG. 9A. When the lever arm 825 is pressed downward, the rear 815 lever tooth disengages from its current position between splines 830. The tension device 820 forces the lever arm 825 forward until the forward 810 lever tooth engages a spline 830 in front of it. Releasing the lever arm 825 enables the rear tooth 815 to engage a spline 830 immediately forward of its last position while being pushed into place by the leaf spring 835. Forward movement of the lever arm 825 causes the coupled roller 830 to squeeze the bladder (not shown) and to dispense the fluid agent within.

Figure 11:
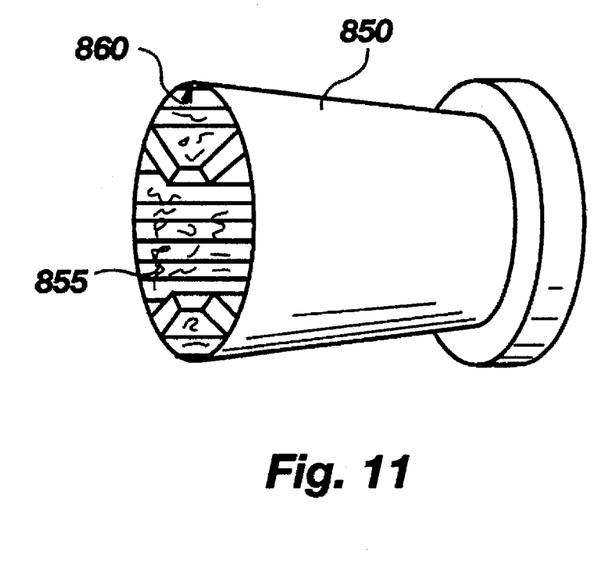
FIG. 11 is a perspective view of a prophy cup.

An alternative embodiment of the present invention is the replacement of the fluid agent in the storage container by a lubricant. A lubricant will be supplied to the prophy cup 850 in the same manner as a prophylactic paste. The fluid agent will not be necessary because the prophy cup 850 will provide an abrasive 855 on the inside cup surface 860. The inside cup surface 860 is normally smooth. The new surface will have an abrasive material 855 coating or embedded within the rubbery prophy cup 850 material. The prophy cup 850 would be easily replaceable when they are worn down or a different grade of abrasive 855 is required. It should also be remembered that a variety of fluids other than lubricants can be dispensed into the prophy cup from the storage and dispensing container.

Figure 12A:
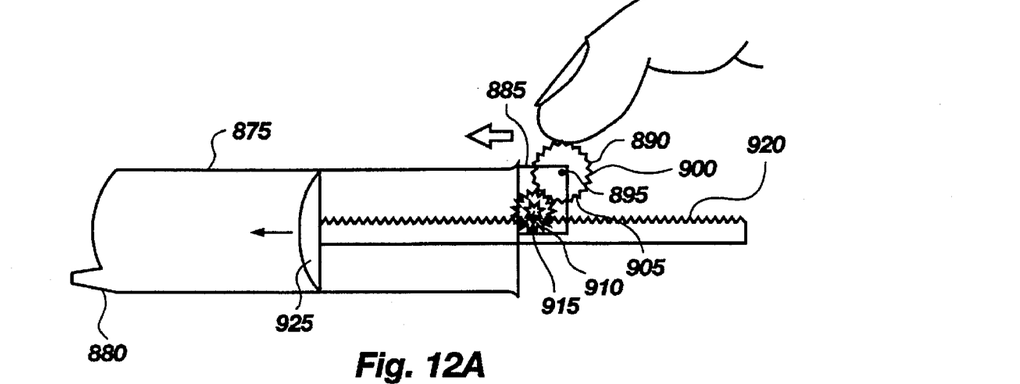
FIG. 12A is an elevational view of an alternative embodiment of FIGS. 4.

An alternative embodiment for a fluid agent storage container is shown in FIG. 12A. The container 875 is a rigid body similar to the syringe embodiment of FIG. 4A. The dispensing orifice 880 has the familiar interference taper to fit snugly into the headpiece container port. The container body 875 includes roller extensions 885 coupled to a filling end. The roller extensions 885 provide a hole 890 into which fits an axle pin 895. Mounted on the axle pin is a primary gear 900 with a plurality of splines 905 around the circumference. The primary gear 900 is in meshing engagement with a splined secondary gear 910, the secondary gear having a tertiary gear 915 on the hub of the secondary gear 910. The splines of the tertiary gear 915 engage splines on a plunger 920. The plunger 920 is formed with an integral wiper 925. The plunger 920 is moved forward when the primary gear 900 is rolled in a forward direction toward the dispensing orifice as indicated by the arrows showing the direction of movement of the gears 900, 910 and 915.

Figure 12B:
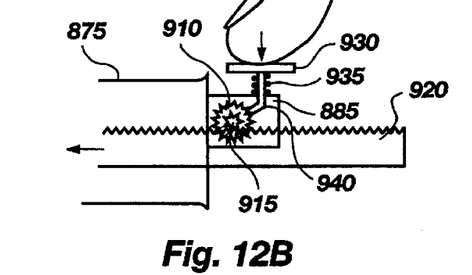
FIG. 12B is a close-up elevational view of an alternative embodiment of FIG. 12A.

A modification of the embodiment of FIG. 12A is shown in the partial elevational cut away view of FIG. 12B. Instead of a primary gear engaging the secondary gear, a push-button 930 with return spring 935 is pressed. The push button 930 has a tooth 940 which engages the splines of the secondary gear 910, the push-button 930 taking the place of the primary gear 900 of FIG. 12A. The return spring 935 compresses against the roller extensions 885, causing the push-button tooth 940 to disengage a spline and reset so as to be in a position to engage another spline and force the secondary gear 910 to repeatedly move the tertiary gear 915 and force the plunger 920 further into the storage container body 875, thereby dispensing a fluid agent contained therein.

Figure 13A:
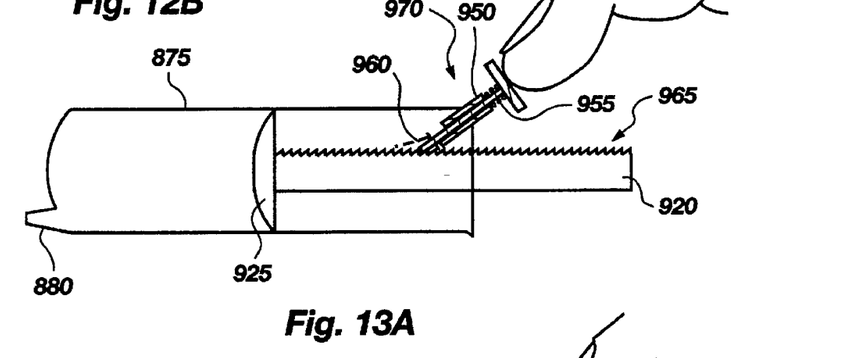
FIG. 13A is an elevational view of an alternative embodiment of FIG. 12A.

The final embodiment of the present invention is shown in FIG. 13A. The syringe body 875 with an interference taper dispensing orifice 880 remain unchanged from FIG. 12. However, instead of a system of gears, an angled push-button drive rod 950 is mounted on the plunger body 875. A similarly ratcheted plunger 920 with integral wiper 925 is also disposed within the syringe 875. A guide bushing 970 holds the drive rod 950, provides a surface for a return spring 955 to compress against, and guides the direction of rod 950 movement. After pressing the drive rod 950 so as to drive the plunger 920 forward, the return spring 955 resets the rod 950, pulling the rod tip 960 backwards along the plunger ratchet 965. It is necessary to make the push-button drive rod 950 with a slightly flexible tip 960 so that the force of pressing the angled rod 950 moves the rod 950 in a forward direction to dispense a fluid agent.

Figure 13B:
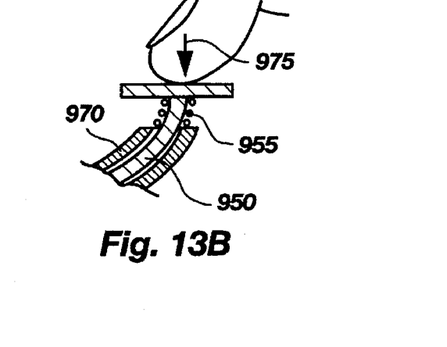
FIG. 13B is a close-up elevational view of an alternative embodiment of FIG. 13A.

A modification of the push-button drive rod 950 of FIG. 13A is shown in the elevational view of FIG. 135. The drive rod 950 is made of a flexible material over its entire length instead of only the tip. This allows a pushing force to be directed in an entirely downward motion, as indicated by the arrow 975.

It is to be understood that the described embodiments of the invention are illustrative only, and that modifications thereof may occur to those skilled in the art. Accordingly, this invention is not to be regarded as limited to the embodiments disclosed, but is to be limited only as defined by the appended claims herein.

Figure 14:
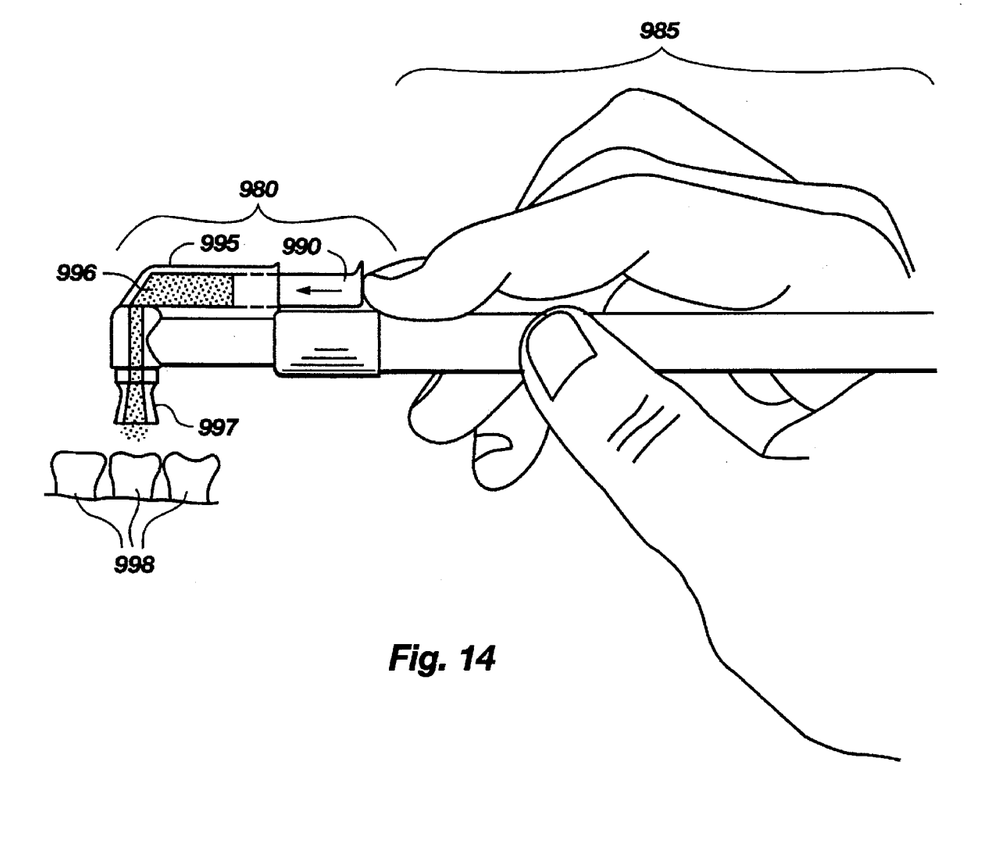
FIG. 14 is an elevational view of the concept of the present invention, showing how the headpiece assembly can be used to dispense a prophylactic paste onto a patient's teeth.

FIG. 14 is an elevational view showing how a typical headpiece assembly 980 of the present invention, coupled to a dental instrument handpiece 985, is used to dispense a fluid 996. A person holds the handpiece 985 and uses a finger or thumb to press on the manual actuation plunger 990 or lever of a fluid storage container 995 that is coupled to the headpiece assembly 980 to dispense a fluid 996 stored therein. The fluid 996 flows from the fluid storage container 995 through the headpiece assembly 980 to the prophy cup 997, from where it is applied to the patient's teeth 998.

What is claimed is:

1. A removable prophylactic headpiece assembly used in cleaning teeth, said headpiece comprising:

a removable headpiece with an attaching end, a top surface, and a working end, having a central bore beginning at the attaching end and extending therethrough along a lengthwise axis defining a drive bore;

a prophy cup bore extending through the removable headpiece at generally a ninety degree angle relative to the central bore, being fluidly coupled to the central bore at the working end, and defining a prophy cup axis which exits at a prophy cup port at the working end;

a lumen which partially extends into and terminates at a lumen port end within the prophy cup bore, opposite to the prophy cup port, and parallel to the prophy cup axis, wherein the lumen defines a hollow passage that exits the headpiece at a container port at the top surface of the headpiece;

a dispensing container coupled to the container port;

said top surface of the headpiece providing a support means for resting the dispensing container thereon, said support means extending generally the length of the headpiece; and a securing means for coupling the dispensing container to the top surface support means to enable a manually operable dispensing actuator to dispense a fluid from said dispensing container.

2. The removable headpiece assembly as defined in claim 1, wherein the support means comprises a trough-shaped shelf.

3. The removable headpiece assembly as defined in claim 1, wherein the dispensing container securing means comprises a plurality of securing pins, said pins being spaced apart, having knobbed ends, and attached to the headpiece top surface proximate to the attaching end.

4. The removable headpiece assembly as defined in claim 3, wherein the plurality of securing pins comprise two parallel pins.

5. The removable headpiece assembly as defined in claim 3, wherein the dispensing container comprises a removable fluid dispenser, said fluid dispenser comprising a container with an end cap at a dispensing end, flexible sidewalls connected to said end cap and forming a tube with an ellipsoid cross-section, a dispensing orifice protruding from said end cap, and a sealed end with a hole punched through said sealed end for securing the fluid dispenser to the headpiece securing pins.

6. The fluid dispenser as defined in claim 5, wherein the dispensing orifice tapers to an interference fit narrowing at a rate of approximately 0.060 inch/inch.

7. The fluid dispenser as defined in claim 5, wherein the dispensing orifice is offset toward an edge of the end cap.

8. The fluid dispenser as defined in claim 5, wherein the sealed end is created by sealing the flexible sidewalls such that a planar surface is formed that is parallel to a plane defined by the top surface.

9. The fluid dispenser as defined in claim 5, wherein the ellipsoid cross-section of the tube is an oval.

10. The removable headpiece assembly as defined in claim 3, wherein the dispensing container further comprises a removable fluid dispenser, said dispenser comprising:
a syringe with a face and an ellipsoid body, wherein the face has a dispensing orifice; and
a plunger in sliding engagement with the syringe, having a body with a ribbed cross-section, and a bottom rib having a beaded edge that couples to the securing pins by pushing the beaded rib edge between the securing pins.

11. The fluid dispenser as defined in claim 10, wherein the plunger has an integral wiper.

12. The fluid dispenser as defined in claim 10, wherein the syringe body further comprises a finger gripping surface on a top of the syringe body relative to the top surface.

13. The fluid dispenser as defined in claim 10, wherein the dispensing orifice comprises a tube which tapers to an interference fit narrowing at a rate of approximately 0.060 inch/inch.

14. The fluid dispenser as defined in claim 13, wherein the dispensing orifice is parallel to the length of the syringe body, and is offset toward an edge of the syringe face.

15. The fluid dispenser as defined in claim 10, wherein the ellipsoid cross-section of the syringe body is an oval.

16. The removable headpiece assembly as defined in claim 3, wherein the dispensing container further comprises a removable fluid dispenser, said dispenser comprising:
a container with an end cap,
flexible sidewalls connected to said end cap and forming a tube with an ellipsoid cross-section,
a dispensing orifice protruding from said end cap and a sealed end with a hole punched through said sealed end for securing the fluid dispenser to the headpiece securing pins, and
an ellipsoid roller disposed within the container which acts as a floating wiper to dispense a fluid when the ellipsoid roller is pushed from the sealed end toward the dispensing orifice.

17. The removable headpiece assembly as defined in claim 3, wherein the headpiece further comprises a removable fluid dispenser, said dispenser comprising:
an ellipsoid body having a face and a sealed attaching end, wherein the attaching end of the body has a beaded rib extending perpendicular from the attaching end of the body along the lengthwise axis for securing the ellipsoid body to the headpiece securing pins;
a floating wiper disposed within the ellipsoid body at its attaching end, wherein the body has a pocket of pressurized gas between the attaching end of the body and the wiper;
a dispensing orifice coupled to the face of the ellipsoid body comprising an interference tapered tube coupled to a shaft, the ellipsoid body sliding partially forward and backward over said shaft to respectively unseal and seal a valve at an end of the shaft within the ellipsoid body to enable dispensing of a fluid.

18. The fluid dispenser as defined in claim 17, wherein the shaft has a first ridge encircling an end within the ellipsoid body, the first ridge being wider than the shaft, a second ridge at a juncture of the interference tapered tube and the shaft, a valve comprising a plurality of ducts adjacent to the first ridge, a sealing ring within the ellipsoid body and surrounding the shaft at a juncture of the moveable shaft and said body, said ring unsealing the ducts when the ellipsoid body is pushed forward and sealing the ducts and pressing against the first ridge when the ellipsoid body moves backward, and a bellows gasket attached at one end to the second ridge and at another end to the ellipsoid body face, said gasket compressing when the ellipsoid body moves forward, and said gasket providing an expanding force causing the ellipsoid body to move backward to seal the ducts when the ellipsoid body is released.

19. The removable headpiece assembly as defined in claim 1, wherein the lumen further comprises a rigid tube having an interference taper beginning at the container port and reducing in diameter at a rate of approximately 0.060 inch/inch, the lumen then turning at an angle until aligned with the lumen port end, and the lumen then having a uniform diameter until it exits at the lumen port end of the prophy cup bore.

20. The removable headpiece assembly as defined in claim 1, wherein the central bore tapers inward to a smaller diameter at approximately a median of the headpiece to define a small central bore nearer the working end and a large central bore nearer the attaching end.

21. The removable headpiece assembly as defined in claim 20, wherein the device further comprises:
a gear shaft mounted for rotation within the small bore, having a smaller diameter coupling shaft extending through and centered within the large central bore, and having a gear on an end of the gear shaft opposite the coupling shaft; and
a plurality of projections extending inward from sidewalls of the small central bore near the median of the headpiece so as to secure the gear shaft within a region defined by said small central bore.

22. The removable headpiece assembly as defined in claim 20, wherein the device further comprises an attachable dental instrument handpiece with an attaching means for securing the coupling shaft to a servomechanism of the dental instrument to provide power to said coupling shaft.

23. The removable headpiece assembly as defined in claim 22, wherein the attaching end has a notch so as to guide placement of the headpiece on to the attachable dental instrument handpiece.

24. The removable headpiece assembly as defined in claim 1, wherein the headpiece further comprises a trough-shaped shelf with two raised sidewalls, each having a slot with a lower and upper edge creating a track through each sidewall and being parallel to the trough-shaped shelf, the lower edge of the slots having splines with edges perpendicular to the lengthwise axis, and a roller disposed on the shelf, having a splined projection on opposite sides of the roller for meshing with the lower edge splines of the slots, each roller projection extending partially into a slot so as to rest upon the slot tracks and provide a support surface for the roller.

25. The removable headpiece assembly as defined in claim 24, wherein the roller is ellipsoid in shape.

26. The removable headpiece assembly as defined in claim 1, wherein the dispensing container further comprises a removable fluid dispenser, said dispenser comprising:

a syringe with an outer face, an inner face with an attached spring mounted in a center of the inner face, an open end, and a body having an ellipsoid cross section, wherein there is a dispensing orifice through the inner and outer faces, a floating ellipsoid shaped wiper at the open end of the syringe with an outer edge and a hole through a center, the hole formed so as to allow a plunger to slide freely therethrough;

a washer mounted on an outer surface of the floating wiper having inner teeth projecting toward a centered washer hole such that the inner teeth also surround the hole in the floating wiper, forming a washer hole smaller in diameter than the hole in the wiper, and having outer teeth that project slightly beyond the outer edge of the wiper so as to create an ellipsoid shape slightly larger than the wiper; and said plunger having a circular cross section, and being coupled to a free end of the spring which is coupled to the inner face, and extending through the hole in the wiper and mounted washer.

27. The removable headpiece assembly as defined in claim 1, wherein the dispensing container further comprises a removable fluid dispenser, said dispenser comprising:

a syringe with an outer face, an inner face with a guiding means mounted in the center of the inner face for guiding forward and backward motion of a plunger coupled in sliding engagement therewith, a sealed end, and an inner body having an ellipsoid cross section, wherein there is a dispensing orifice through the inner and outer faces, a floating wiper at the open end of the syringe with an outer edge and a hole through a center the hole formed so as to allow the plunger to slide freely therethrough;

a washer mounted on an outer surface of the floating wiper having inner teeth projecting toward a centered washer hole such that the inner teeth also surround the hole in the floating wiper, forming a washer hole smaller in diameter than the hole in the wiper, and having outer teeth that project slightly beyond the outer edge of the wiper so as to create an ellipsoid shape slightly larger than the wiper; and said plunger having a circular cross section and coupled in sliding engagement with the guiding means, and extending through the hole in the wiper and mounted washer.

28. The removable headpiece assembly as defined in claim 1, wherein the headpiece further comprises:

a trough-shaped shelf with raised sidewalls, wherein there is a slot through each sidewall, the slot having a lower and upper edge creating a track parallel to the trough-shaped shelf, the upper edge of the slots having splines with edges perpendicular to the headpiece lengthwise axis, a roller with an axle resting on each lower edge, a finger lever forming an arch, wherein ends of the arch form heads, each head having a lever tooth, a leaf spring and a pivot point, each head resting within one of said slot tracks, the pivot points having the roller axle disposed therein, such that applied pressure forces the lever downward, each lever tooth engaging a spline causing the pivot points to move forward along the track and drive the roller forward, and such that releasing pressure on the lever causes the leaf springs to engage the slot tracks and for each lever tooth to engage an adjacent forward spline.

29. The removable headpiece assembly as defined in claim 1, wherein the headpiece further comprises:

a trough-shaped shelf with raised sidewalls, wherein there is a slot through each sidewall, the slot having a lower and upper edge creating a track parallel to the shelf, the upper edge of the slots having splines which are perpendicular to the headpiece lengthwise axis, a roller with an axle resting on each lower edge, a finger lever forming an arch, wherein ends of the arch form heads, each head with a first and second lever tooth, a leaf spring, a pivot point and a tension device, each head resting within one of said slot tracks, the pivot points having the roller axle disposed therein, such that applied pressure forces the lever downward, the first lever teeth disengaging from splines enabling the heads to be drawn forward with the roller until the second teeth engage a first immediately adjacent forward spline of a past spline position, and such that releasing pressure on the lever causes the leaf springs to engage the slot tracks and reset the lever by pulling the second lever teeth from a spline and engaging the first lever teeth in a second immediately adjacent forward spline.

30. A removable headpiece assembly as defined in claim 1, wherein a prophy cup is coupled to the working end, said prophy cup having a surface with an abrasive material partially embedded therein, and having an aperture formed in the prophy cup whereby a fluid for lubrication can be passed to said prophy cup.

31. The removable headpiece assembly as defined in claim 1, wherein the dispensing further comprises a removable fluid dispenser, said dispenser comprising:

a syringe with a face, an ellipsoid body and a fluid insertion end, wherein the face has a dispensing orifice therethrough;

a plunger in sliding engagement with the syringe, wherein the plunger has a rigid body with a top surface having a plurality of splines;

a manually operable plunger advancement means for engaging the plurality of plunger splines and incrementally moving the plunger forward in the syringe body so as to force a fluid from the dispensing orifice.

32. The fluid dispenser as defined in claim 31, wherein the manually operable plunger advancement means comprises:

a pair of opposing syringe body extension members coupled to the fluid insertion end with an opposing hole through each extension member;

a first circular rotating gear on a first axle, said first axle disposed in the opposing holes of the extension members;

a second gear in meshing engagement with the first gear, having a third gear forming a second axle for the second gear, the third gear engaging the plurality of top surface plunger splines so that rolling the first gear in the proper direction causes the plunger to move forward toward the plunger face.

33. The fluid dispenser as defined in claim 31, wherein the manually operable plunger advancement means comprises:

a pair of opposing syringe body extension members coupled to the fluid insertion end and forming a guide bushing;

a pushing rod mounted in sliding engagement within the guide bushing, having a tooth on a gear engaging end, and a pushing surface on an opposing end;

a spring encircling the pushing rod and disposed so as to compress against a top surface of the guide bushing and a bottom surface of the rod pushing surface;

a first gear in meshing engagement with the pushing rod tooth, having a second gear forming an axle for the first gear, the second gear engaging the plurality of top surface plunger splines so that pressing on the pushing surface causes the plunger to move toward the plunger face.

34. The fluid dispenser as defined in claim 31, wherein the manually operable plunger advancement means comprises:

a guide bushing mounted on the fluid insertion end at an angle toward a center axis of the syringe body;

a pushing rod disposed within said guide bushing, having an angled pushing surface mounted on a pushing end, and a flexible tip which engages the plunger splines;

a spring encircling the pushing rod and disposed so as to compress against a top surface of the guide bushing and a bottom surface of the rod pushing surface.

35. The fluid dispenser as defined in claim 31, wherein the manually operable plunger advancement means comprises:

a guide bushing mounted on the fluid insertion end at an angle toward a center axis of the syringe body;

a flexible pushing rod disposed within said guide bushing, having a pushing surface mounted on a pushing end, and a tip which engages the plunger splines, said pushing surface being perpendicular to a lengthwise axis of the syringe body;

a spring encircling the pushing rod and disposed so as to compress against a top surface of the guide bushing and a bottom surface of the rod pushing surface.

36. The removable prophylactic headpiece assembly used in cleaning teeth as defined in claim 1, wherein the dispensing container may be filled with materials selected from the group consisting of prophylactic cleaning agents, prophy paste, lubricants and fluids of various viscosities.

* * * * *